US010591559B2

(12) United States Patent
You et al.

(10) Patent No.: US 10,591,559 B2
(45) Date of Patent: Mar. 17, 2020

(54) RADIO-FREQUENCY COIL APPARATUS AND BASE HAVING A SLIDING AND COIL MANAGEMENT SYSTEM

(71) Applicant: Siemens Healthcare GmbH, Erlangen (DE)

(72) Inventors: Jun You, Shenzhen (CN); Zeng He He, Shenzhen (CN); Stephan Zink, Erlangen (DE); Volker Matschl, Bamberg (DE); Wen Ming Li, Shenzhen (CN); Rainer Kurth, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 57 days.

(21) Appl. No.: 15/910,488

(22) Filed: Mar. 2, 2018

(65) Prior Publication Data

US 2018/0252782 A1    Sep. 6, 2018

(30) Foreign Application Priority Data

Mar. 2, 2017    (CN) ...................... 2017 2 0201724 U

(51) Int. Cl.
*G01R 33/34* (2006.01)
*G01R 33/3415* (2006.01)
*G01R 33/36* (2006.01)
*A61B 5/055* (2006.01)

(52) U.S. Cl.
CPC . *G01R 33/34092* (2013.01); *G01R 33/34007* (2013.01); *G01R 33/3415* (2013.01); *G01R 33/36* (2013.01); *A61B 5/055* (2013.01)

(58) Field of Classification Search
CPC ........ G01R 33/34092; G01R 33/34007; G01R 33/36; G01R 33/3415; A61B 5/055
See application file for complete search history.

(56) References Cited

U.S. PATENT DOCUMENTS

| 4,587,493 | A | * | 5/1986 | Sepponen | ........ G01R 33/34007 324/318 |
| 4,684,894 | A | * | 8/1987 | Bliehall | ................ G01R 33/341 324/300 |
| 2013/0225980 | A1 | * | 8/2013 | Biber | .................... A61B 5/055 600/422 |
| 2016/0238677 | A1 | * | 8/2016 | Fischer | .................. A61B 5/055 |

* cited by examiner

*Primary Examiner* — G. M. A Hyder
(74) *Attorney, Agent, or Firm* — Schiff Hardin LLP

(57) ABSTRACT

Radio-frequency (RF) coil apparatus for magnetic resonance imaging has a base and an RF coil, wherein the base has a sliding base guide structure and a guide cavity, the RF coil has a sliding coil structure fitting the sliding base guide structure, and an electric cable of the RF coil is accommodated in the guide cavity and can move in the guide cavity. One end of the electric cable is fixed to the RF coil by a first fixing bracket, and another end of the electric cable is fixed to the base by a second fixing bracket so that a predetermined length of the cable projects from the base.

13 Claims, 8 Drawing Sheets

RADIO-FREQUENCY COIL APPARATUS AND BASE HAVING A SLIDING AND COIL MANAGEMENT SYSTEM

BACKGROUND OF THE INVENTION

Field of the Invention

The present invention is in the technical field of nuclear magnetic resonance imaging, in particular a radio-frequency coil apparatus and a base.

Description of the Prior Art

Magnetic resonance imaging (MRI) is a tomographic modality that uses the phenomenon of magnetic resonance to obtain an electromagnetic signal from the human body, and to reconstruct human body information. An MRI apparatus uses MRI imaging technology to display anatomical and pathological sectional images of different structures in different shades of gray, and is widely used in the medical and health fields, to help doctors in the diagnosis of illnesses.

An MRI apparatus has a radio-frequency (RF) coil apparatus. FIG. 1 is a top view of a conventional RF coil apparatus. As FIG. 1 shows, the RF coil apparatus has an RF coil 1 and a base 2. The RF coil 1 is positioned on the base 2, and the base 2 has a sliding guide structure 21, a sliding structure (not shown in FIG. 1) fitting the sliding guide structure 21 is provided on the RF coil 1, so the RF coil 1 can slide on the base 2 along the sliding guide structure 21. An electric cable 3 of the RF coil 1 is positioned outside the RF coil apparatus. In order to insert the plug on a free end of the electric cable into a power supply socket located in a fixed position on a patient support table, the only option is to press the electric cable beneath the patient's body.

Taking a knee RF coil apparatus as an example, FIG. 2 is a top view of a known MRI apparatus. As FIG. 2 shows, a patient is lying on the patient support table 4, and the electric cable 3 is positioned on the patient support table 4. In order to insert the plug 31 on a free end of the electric cable into a socket 41 on the patient support table 4, a portion of the electric cable 3 must be pressed beneath the patient's body. Moreover, when the position of the RF coil 1 is adjusted according to the position of the patient's knee, the electric cable 3 pressed beneath the patient's body will obstruct the sliding of the RF coil 1, and might even cause the RF coil 1 to slide out of the sliding guide structure 21. Furthermore, dragging the electric cable 3 beneath the patient's body will be painful to the patient.

SUMMARY OF THE INVENTION

In view of the above, the present invention provides an RF coil apparatus and a base, for sliding an RF coil smoothly.

The radio-frequency (RF) coil apparatus according to the invention has a base and an RF coil, wherein the base has a base sliding guide structure and a guide cavity. The RF coil has a coil sliding structure fitting the base sliding guide structure. An electric cable of the RF coil is accommodated in the guide cavity, and can move in the guide cavity. One end of the electric cable is fixed to the RF coil by a first fixing bracket, and another end of the electric cable is fixed to the base by a second fixing bracket so that the cable has a predetermined length projecting from the base.

Preferably, the base also has an electric cable drag chain, the electric cable drag chain being disposed in the guide cavity, and the electric cable drag chain has one end fixed to the RF coil and another end fixed in the base. The electric cable in the guide cavity is sheathed in the electric cable drag chain.

Preferably, a recess is provided in the base, with the bottom of the RF coil being positioned in the recess. Preferably, the apparatus further has a slide rack and an engaging element fitting the slide rack, wherein the slide rack is disposed in a fixed manner on the base. The engaging element is installed on the RF coil so that during sliding of the RF coil along the base sliding guide structure, the engaging element can be engaged in or disengaged from a slot of the slide rack by the action of an external force.

Preferably, the apparatus further comprises: an engaging element locking mechanism installed on the RF coil, and being designed to lock the engaging element when the engaging element is engaged in the slot of the slide rack.

Preferably, the locking mechanism has a stop-plate, a support and a control arm, with the control arm installed on the RF coil in an engaged manner, so as to move in a direction toward or away from the stop-plate. The support is fixed to the RF coil, and the support has a slide groove in which the stop-plate is disposed so as to move up and down in the slide groove. A push-rod at one end of the control arm bears against an inclined face on a side of the stop-plate in order to limit the stop-plate, such that a lower end of the stop-plate bears against a side end face of the engaging element under the action of a downward force, thereby locking a position of the engaging element. The control arm, under the action of an external force, moves along the inclined face on the side of the stop-plate so as to push the stop-plate to move to a position above the engaging element, thereby releasing the locking of the engaging element.

Preferably, the apparatus further has a fixing block, and the aforementioned base guide structure is a first sliding base guide structure.

The base has a second sliding base guide structure with guiding directions of the second sliding guide structure and the first sliding guide structure being the same. The fixing block is installed on the base in an engaged manner, and slides along the second sliding guide structure. The RF coil is connected in a fixed manner to the fixing block.

A base according to the invention has a base main body that has a sliding base guide structure thereon and a guide cavity thereon.

The sliding base guide structure of the base main body is designed to fit a sliding mechanism on an RF coil such that the RF coil can slide on the base main body. The guide cavity is designed to accommodate an electric cable of the RF coil therein, such that the electric cable can move in the guide cavity.

One end of the electric cable is fixed to the RF coil by a first fixing bracket, and the base main body has a second fixing bracket that is positioned relative to the first fixing bracket so as to fix another end of the electric cable to the base main body so as to have a predetermined length of the cable projecting from the base main body.

Preferably, the base further has an electric cable drag chain, the electric cable drag chain being disposed in the guide cavity, and having one end fixed in the base main body and another end configured to be fixed to the RF coil, such that the electric cable is sheathed in the electric cable drag chain.

Preferably, a recess is provided in the base main body, for positioning the bottom of the RF coil.

Preferably, the base further has a fixing block and the aforementioned base guide structure is a first sliding base guide structure.

The base main body also has a second sliding base guide structure with guiding directions of the second sliding guide structure and the first sliding guide structure being the same.

The fixing block is installed on the base main body in an engaged manner, so as to slide along the second sliding guide structure. The fixing block is configured to be connected in a fixed manner to the RF coil.

The base of the RF coil apparatus of the present invention thus has a sliding base guide structure and a guide cavity in the base, the RF coil has a sliding coil structure fitting the sliding base guide structure, and an electric cable of the RF coil is accommodated in the guide cavity, and can move in the guide cavity so a part of the electric cable can be concealed in the base, avoiding the need to press it beneath a patient's body, and enabling smooth sliding of the RF coil.

DESCRIPTION OF THE PREFERRED EMBODIMENTS

In order to explain the objects, technical solution and advantages of the present invention, the present invention is described in detail below in a number of embodiments.

Figure 1:
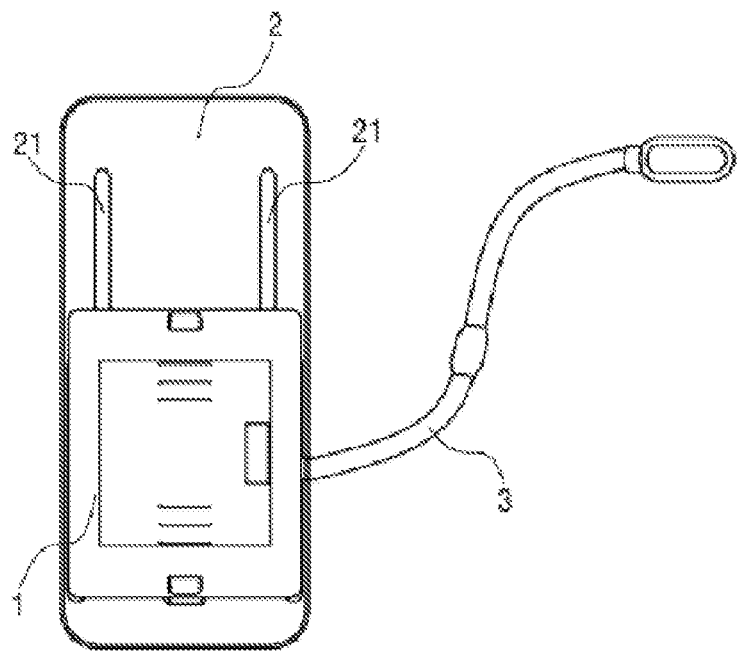
FIG. 1 is a top view of a known RF coil apparatus.
Figure 2:
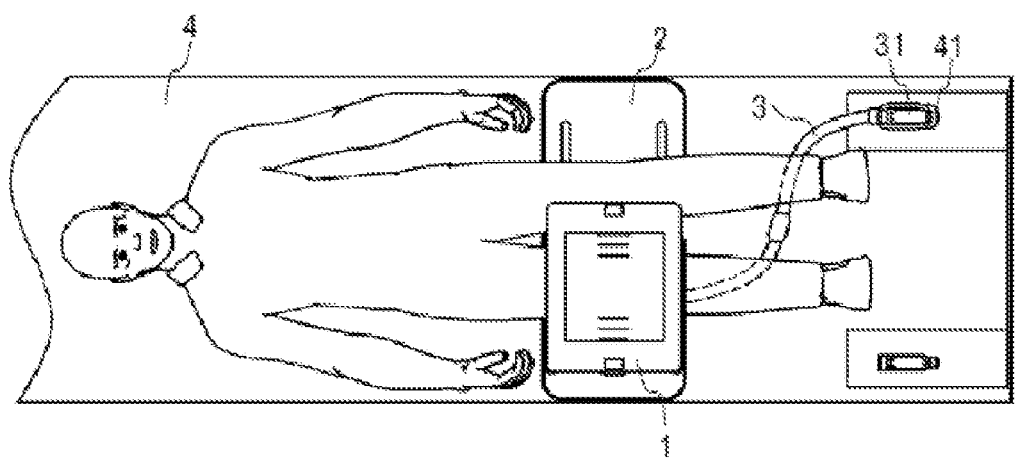
FIG. 2 is a top view of a known MRI apparatus.
Figure 3:
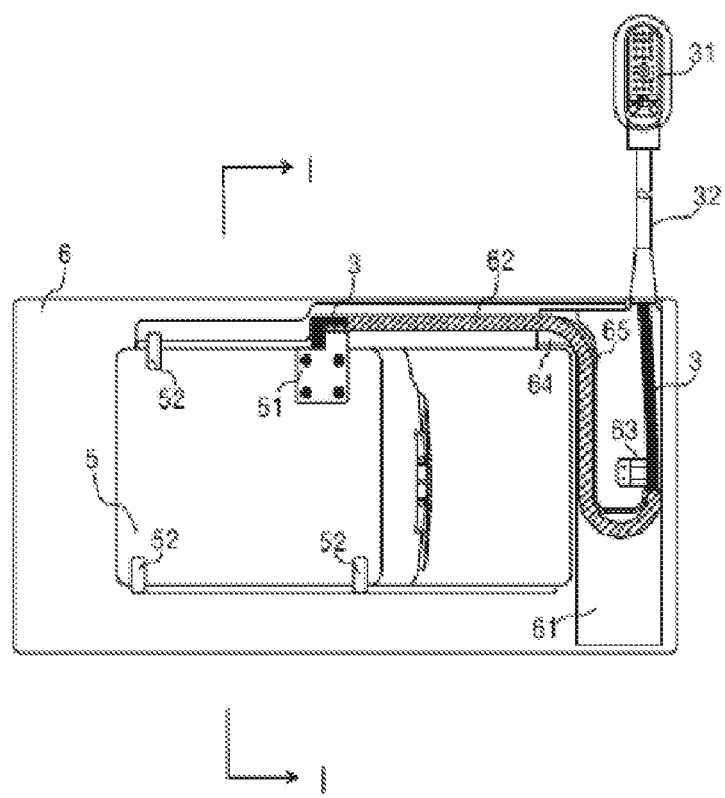
FIG. 3 is a bottom view of an RF coil apparatus according to an embodiment of the present invention when the RF coil is located on one side of the base.
Figure 4:
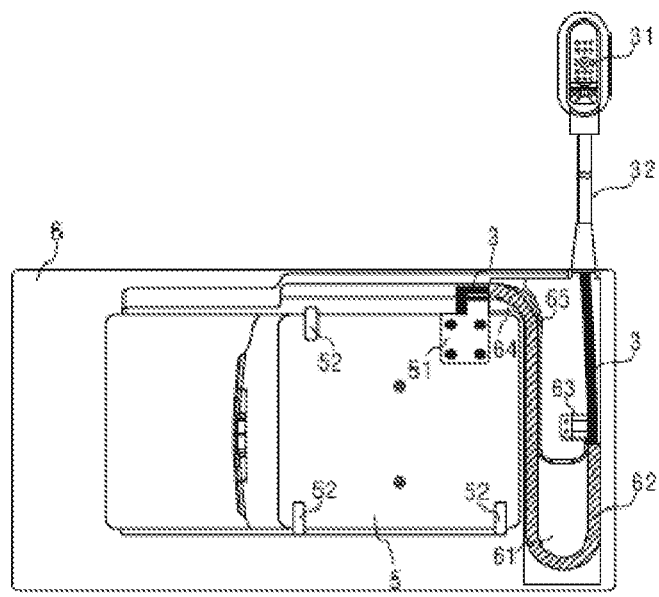
FIG. 4 is a bottom view of the RF coil apparatus according to an embodiment of the present invention when the RF coil is located on another side of the base.
Figure 8:
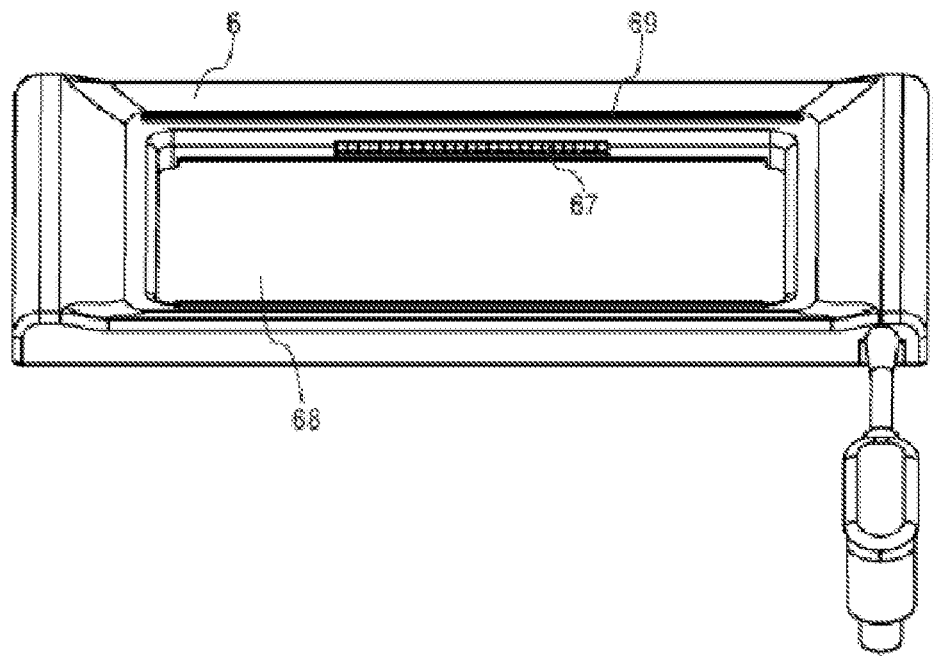
FIG. 8 is a top view of the base in an RF coil apparatus according to an embodiment of the present invention.
Figure 9:
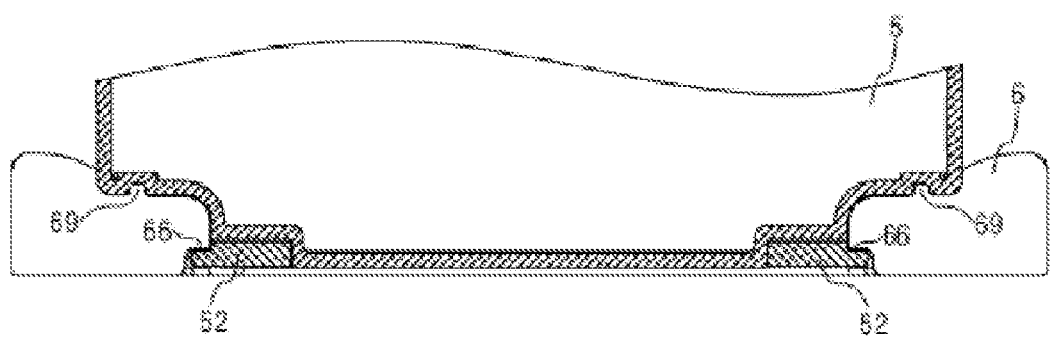
FIG. 9 is a sectional view along I-I of the RF coil apparatus shown in FIG. 3.
Figure 10:
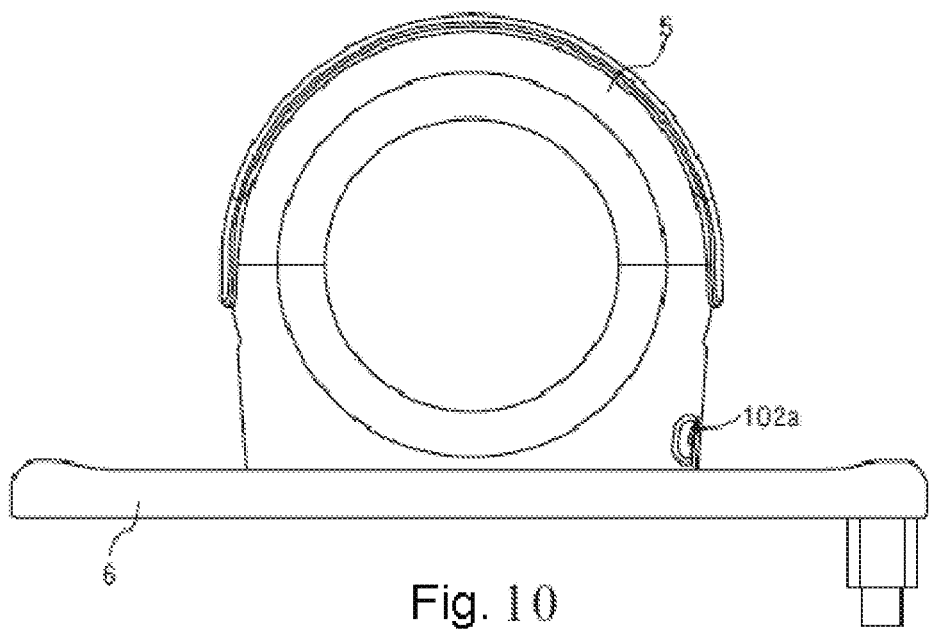
FIG. 10 is a front view of an RF coil apparatus according to an embodiment of the present invention.

FIG. 3 is a bottom view of an RF coil apparatus according to an embodiment of the present invention when the RF coil is located on one side of the base. FIG. 4 is a bottom view of an RF coil apparatus according to an embodiment of the present invention when the RF coil is located on another side of the base. FIG. 8 is a top view of the base in an RF coil apparatus according to an embodiment of the present invention. FIG. 9 is a sectional view along I-I of the RF coil apparatus shown in FIG. 3. FIG. 10 is a front view of an RF coil apparatus according to an embodiment of the present invention.

As shown in FIG. 3, the RF coil apparatus has an RF coil 5 and a base 6. The base 6 has a base sliding guide structure (not shown in FIG. 3) and a guide cavity 61. The RF coil 5 has a sliding structure (not shown in FIG. 3) fitting the base sliding guide structure; an electric cable 3 of the RF coil 5 is accommodated in the guide cavity 61, and can move in the guide cavity 61.

The base 6 has two through-holes (not shown in FIG. 3), namely an inlet and an outlet. A free end of the electric cable 3 passes into the base 6 from one through-hole, the inlet. The free end of the electric cable 3 then passes out from the other through-hole, the outlet. The electric cable 3 outside the base 6 may be sheathed in a tube sleeve, in order to be protected. In other embodiments, the inlet and outlet could also be openings accommodating the passage of the electric cable 3, or could also be other embodiments; no restriction is imposed in this respect.

The base 6 also has an electric cable drag chain 62 disposed in the guide cavity 61. The electric cable drag chain 62 has one end fixed to the RF coil 5 by a fixing connection bracket 51, and another end fixed in the base 6 by a second fixing bracket 63. In this way, the electric cable 3 sheathed in the electric cable drag chain 62 can move smoothly in the guide cavity 61.

As shown in FIGS. 3 and 4, in the guide cavity 61, the position of movement of the electric cable drag chain 62 in the guide cavity 61 can be precisely defined by means of a guide block 64 and a guide track 65. FIG. 3 shows the position of the electric cable 3 in the guide cavity 61 when the RF coil 5 slides to one end of the base 6. FIG. 4 shows the position of the electric cable 3 in the guide cavity 61 when the RF coil 5 moves to another end of the base 6.

In one embodiment, one end of the electric cable is fixed in the RF coil by a first fixing bracket, and another end of the electric cable is fixed in the guide cavity 61 or outside the RF coil apparatus by a second fixing bracket. As shown in FIGS. 3 and 4, one end of the electric cable 3 is fixed in the RF coil 5 by the fixing connection bracket 51 (first fixing element). Another end of the electric cable 3 located in the base 6 is fixed in the guide cavity 61 by the second fixing bracket 63 (second fixing element) so that a predetermined length of the cable 3 projects from the base 6. Alternatively, another end of the electric cable 3 located outside the RF coil apparatus could also be sheathed in an electric cable sheath 32 (second fixing element) of a definite length, in order to be fixed on one side of the patient table (not shown in the figure), and not move with the RF coil apparatus. Since the electric cable projecting from the base is of short length and is fixed on one side of the patient table, remote from the patient's body, it will not affect the comfort of the patient's body. Moreover, since the cable projecting from the base is of short length, there is no need for an RF choke resonator to be additionally provided on this section of electric cable, so that this section of electric cable is lightweight and RF signals are stable. Furthermore, when the RF coil is installed on the base, this section of cable of short length can also help an operator to quickly and accurately determine the position of the RF coil on the base.

Figure 5:
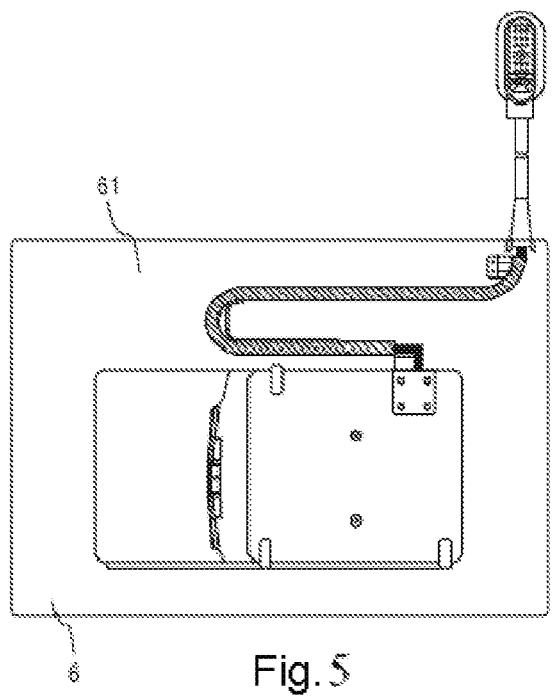
FIG. 5 is a bottom view of an RF coil apparatus according to an embodiment of the present invention, with the guide cavity located in another position in the base.
Figure 6:
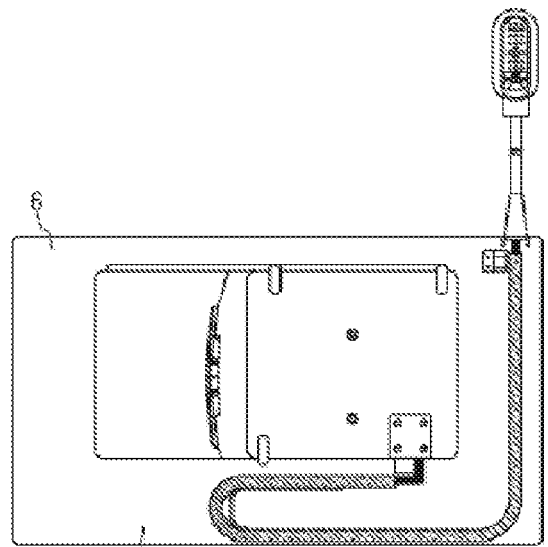
FIG. 6 is a bottom view of an RF coil apparatus according to an embodiment of the present invention, with the guide cavity located in another position in the base.

In other embodiments, the guide cavity 61 could also be disposed in another position in the base 6. For example, FIGS. 5 and 6 show schematic diagrams of the guide cavity 61 disposed in different positions on the base 6. The present invention does not define the specific position in which the guide cavity 61 is disposed.

Figure 7:
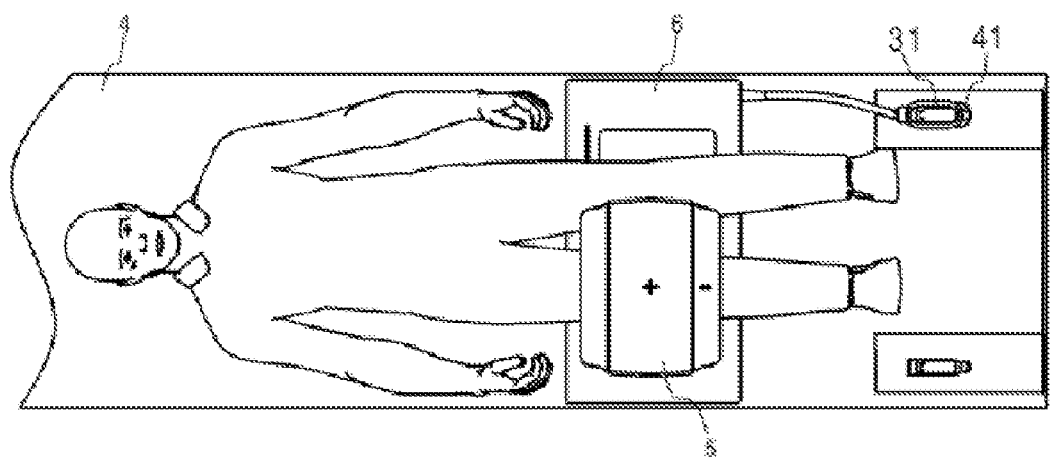
FIG. 7 is a top view of an MRI apparatus according to an embodiment of the present invention.

FIG. 7 is a top view of an MRI apparatus according to an embodiment of the present invention. As FIG. 7 shows, in the RF coil apparatus provided on the basis of an embodiment of the present invention, when the RF coil 5 slides on the base 6 along the base sliding guide structure, the electric cable 3 located outside the base is positioned in a fixed manner on the power supply socket side of the patient support table 4.

In a known RF coil apparatus, the bottom of the RF coil is positioned on the base. As a result, the center of the RF coil is remote from the center of a shimming region, so the imaging quality of images is affected.

As shown in FIG. 8, a recess 68 is provided in the base 6, and the bottom of the RF coil 5 is positioned in the recess 68. As a result, the center of the RF coil is closer to the center of the shimming region, so the imaging quality of images is improved.

It should be noted that the base provided with the recess can not only be used in cooperation with the RF coil apparatus in the present invention, but could also be used in cooperation with an existing RF coil apparatus; the present invention does not impose any restriction in this respect.

As shown in FIG. 9, the bottom of the RF coil 5 is positioned in the recess provided in the base 6. The RF coil apparatus may also have a fixing block 52. As shown in FIG. 9, the base 6 has a second sliding guide structure 66. The guide directions of the second sliding guide structure 66 and the base sliding guide structure 69 are the same. The fixing block 52 is installed on the base 6 in an engaged manner, and can slide along the second sliding guide structure 66. The RF coil 5 is connected in a fixed manner to the fixing block 52.

It should be noted that the base provided with the recess can not only be used in cooperation with the RF coil apparatus provided in the present invention, but could also be used in cooperation with an existing RF coil apparatus; the present invention does not impose any restriction in this respect.

In a known RF coil apparatus, a slide rack is disposed on the base; the rack fits an engaging element that is already installed on the RF coil. When the RF coil slides along the sliding guide structure, the engaging element can be engaged in or disengaged from slots of the slide rack under the action of an external force. However, there is no locking function between the slide rack and the engaging element. The engaging element can be engaged in or disengaged from the slots of the slide rack as long as an external force is applied to the engaging element. Thus, if an external force is applied to the engaging element by mistake during device operation, this will cause sliding of the RF coil, affecting the imaging result.

Figure 11:
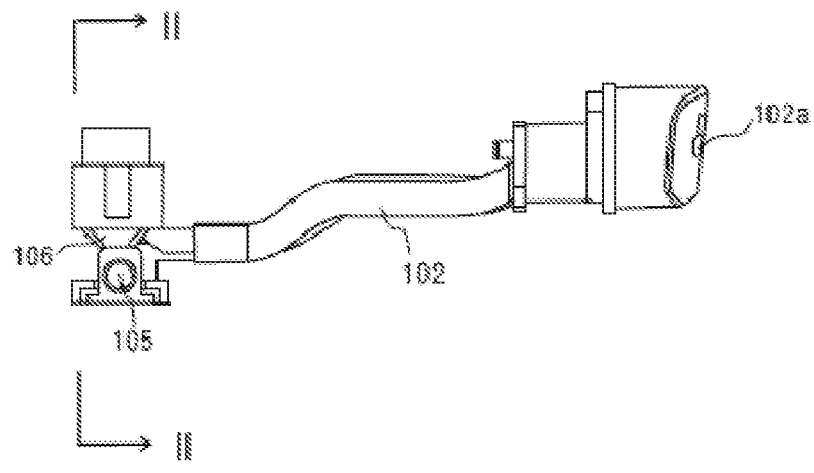
FIG. 11 shows an engaging element locking mechanism, disposed on one side of the RF coil apparatus, according to an embodiment of the present invention.
Figure 12:
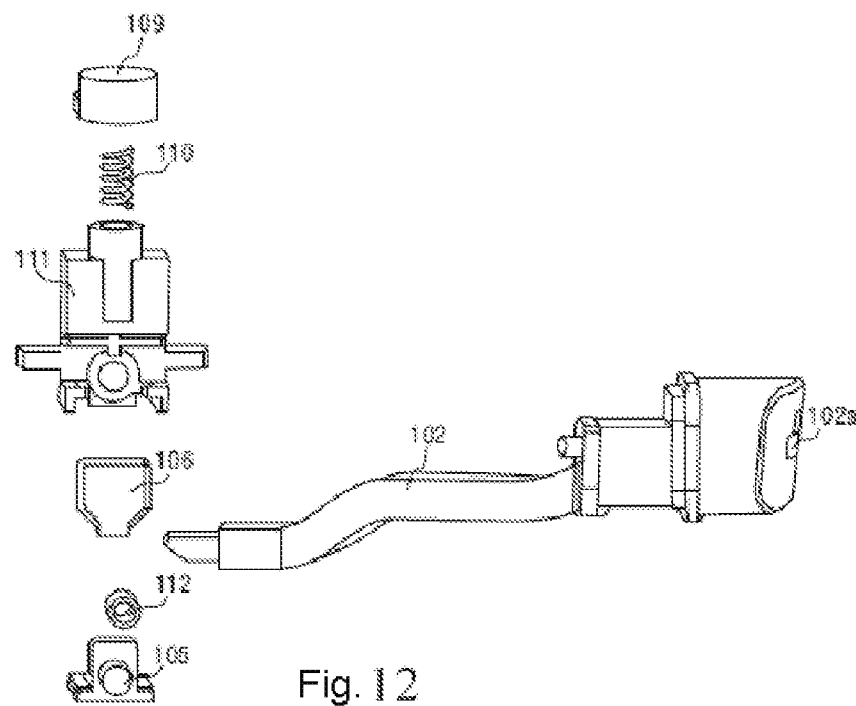
FIG. 12 is an exploded view of the engaging element locking mechanism, disposed on one side of the RF coil apparatus, according to an embodiment of the present invention.
Figure 13:
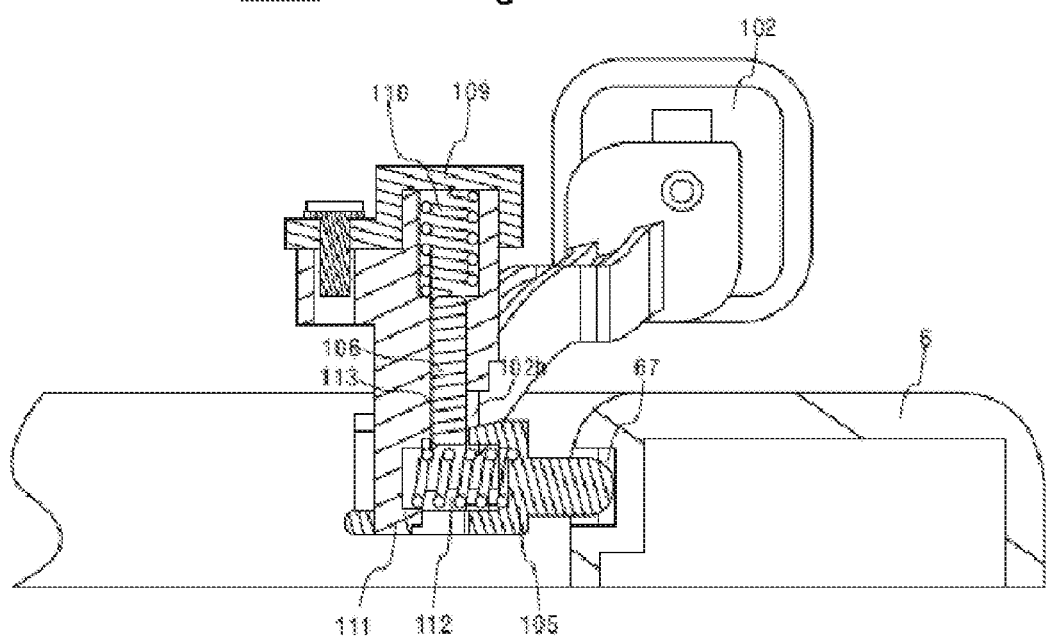
FIG. 13 is a sectional view along II-II when the engaging element locking mechanism shown in FIG. 11 is in a locked state.
Figure 14:
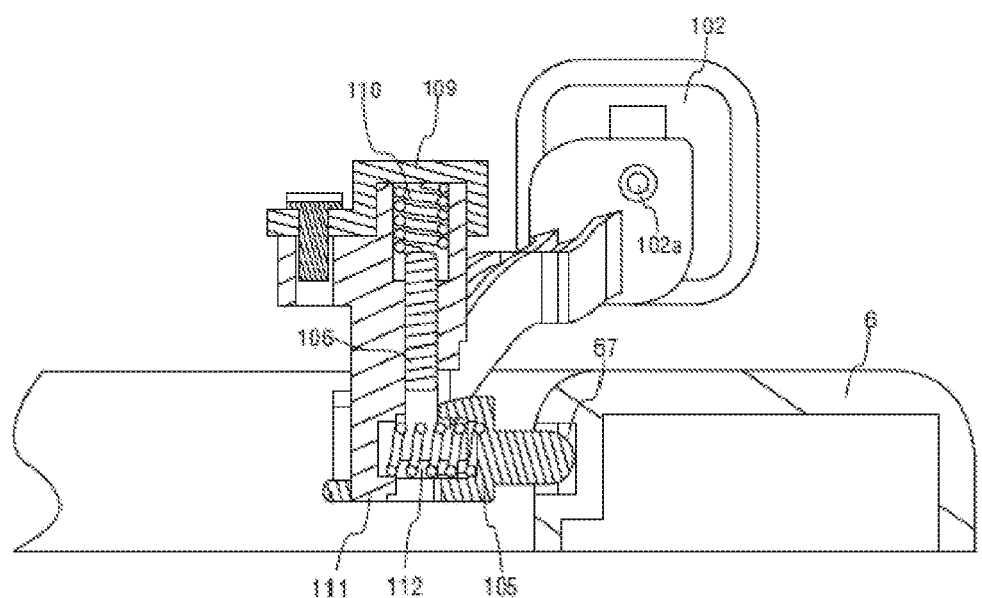
FIG. 14 is a sectional view along II-II when the engaging element locking mechanism shown in FIG. 11 is in an unlocked state.

FIG. 11 is a main view of an engaging element locking mechanism, disposed on one side of the RF coil apparatus, according to an embodiment of the present invention. FIG. 12 is a structural exploded view of an engaging element locking mechanism, disposed on one side of the RF coil apparatus, according to an embodiment of the present invention. FIG. 13 is a sectional view along II-II when the engaging element locking mechanism shown in FIG. 11 is in a locked state. FIG. 14 is a sectional view along II-II when the engaging element locking mechanism shown in FIG. 11 is in an unlocked state.

As shown in FIGS. 8 and 11, a slide rack 67 is installed on the base. The engaging element locking mechanism is installed at the bottom of the RF coil, and can be used to lock an engaging element 105 when the engaging element 105 is engaged in a slot of the slide rack 67. An unlocking push-button 102a is provided on a housing of the RF coil 5; by pressing the unlocking push-button 102a, the locking of the engaging element 105 can be released.

The control arm 102 is installed on the RF coil 5 in an engaged manner, and can move in a direction towards or away from the stop-plate. The support 111 is fixed to the RF coil 5. As FIGS. 13 and 14 show, the support 111 has a slide groove 113; the stop-plate 106 is disposed in the slide groove 113, and can move up and down in the slide groove 113.

As shown in FIG. 13, in a locked state, a push-rod 102b at one end of the control arm 102 bears against an inclined face on a side of the stop-plate 106 in order to limit the stop-plate 106 (as shown in FIG. 11). A first spring 110 is installed above the stop-plate 106, and covered by a spring cap 109. The first spring 110 above the stop-plate 106 applies a downward elastic force thereto, such that a lower end of the stop-plate 106 bears against a side end face of the engaging element 105 under the joint action of the downward elastic force and gravity, thereby locking the position of the engaging element 105. A second spring 112 is disposed on a left side of the engaging element 105. The second spring 112 applies an elastic force to the engaging element 105, so that the engaging element 105 can bear against an inner side of a slot of the slide rack 67.

As shown in FIG. 14, in an unlocked state, an external force is applied to the unlocking push-button 102a on one side of the control arm 102; the external force causes the control arm 102, moving along the inclined face on the side of the stop-plate, to push the stop-plate 106 to move upwards to a position above the engaging element 105, thereby releasing the locking of the engaging element 105. When application of the external force is stopped, the stop-plate 106 moves downwards under the action of gravity and the elastic force of the first spring 110, such that the lower end of the stop-plate bears against the side end face of the engaging element 105 again, and the engaging element locking mechanism is in a locked state again.

Figure 15:
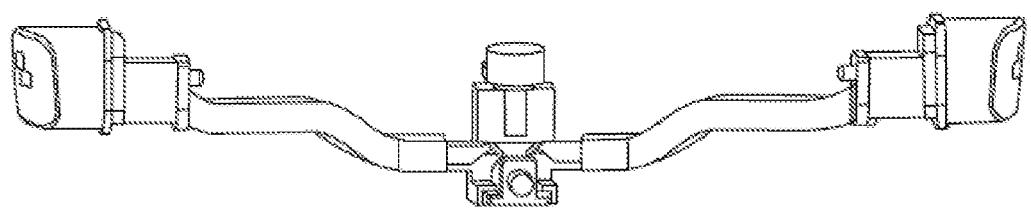
FIG. 15 shows engaging element locking mechanism, disposed on two sides of the RF coil apparatus, according to an embodiment of the present invention.

FIG. 15 is a main view of an engaging element locking mechanism, disposed on two sides of the RF coil apparatus, according to an embodiment of the present invention. As shown in FIG. 15, another engaging element locking mechanism and the locking mechanism described above are symmetrical in structure, and are disposed opposite one another on the RF coil apparatus.

It should be noted that the engaging element locking mechanism described above can not only be used in cooperation with the RF coil apparatus provided in the present invention, but could also be used in cooperation with an existing RF coil apparatus; the present invention does not impose any restriction in this respect.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:
1. A radio-frequency (RF) coil apparatus comprising:
a base configured to be disposed on top of a patient table, the base having a sliding base guide structure thereon and a guide cavity therein;
an RF coil having a sliding coil structure fitting the sliding base guide structure and having an electric cable, connected to the RF coil, accommodated in the guide cavity of the base so as to move in the guide cavity; and a first fixing bracket that fixes one end of the electric cable to the RF coil, and a second fixing bracket that fixes an opposite end of the electric cable to the base, with said first and second fixing brackets having a spacing therebetween and being positioned relative to each other so as to make a predetermined length of said electric cable project from the base.

2. An RF coil apparatus as claimed in claim 1 wherein said base comprises an electric cable drag chain disposed in the guide cavity, said electric cable drag chain having one end thereof fixed to the RF coil and another end thereof fixed to the base, said electric cable being sheathed in the guide cavity by the electric cable drag chain.

3. An RF coil apparatus as claimed in claim 1 wherein said base comprises a recess, and wherein a bottom of said RF coil is positioned in said recess.

4. An RF coil apparatus as claimed in claim 1 comprising:
a slide rack and an engaging element fitting the slide rack, said slide rack being fixedly mounted on the base, and said slide rack having a slot therein; and
said engaging element being installed on the RF coil at a position that, during sliding of the RF coil along the sliding base guide structure, causes the engaging element to be engaged in or disengaged from said slot, by action of an externally applied force.

5. An RF coil apparatus as claimed in claim 4 comprising an engaging element locking mechanism installed on the RF coil and locking the engaging element when the engaging element is engaged in said slot of the slide rack.

6. An RF coil apparatus as claimed in claim 5 wherein said locking mechanism comprises:
a stop plate;
a support fixed to the RF coil and having a slide groove therein;
a control arm that engages said RF coil and is movable in respective directions toward and away from said stop plate;
said stop plate being disposed in said slide groove so as to be movable up and down in said slide groove;
a push rod situated at an end of the control arm and bearing against an inclined face at a side of said stop plate so as to limit said stop plate, said stop plate having a lower end that bears against a side end face of the engaging element under action of a downward force, so as to lock a position of the engaging element; and
said control arm, in response to said externally applied force, moving along said inclined face on the side of the stop plate and pushing the stop plate so as to move the stop plate to a position above the engaging element, thereby releasing said blocking of said engaging element.

7. An RF coil apparatus as claimed in claim 1 wherein said sliding base guide structure is a first sliding base guide structure, having a guiding direction, and wherein said RF coil apparatus comprises:
a second sliding base guide structure on said base, said second sliding base guide structure having a guiding direction that is the same as the guiding direction of the first sliding base guide structure;
a fixing block installed on said base so as to slide along said second sliding base guide structure; and
said RF coil being fixedly connected to said fixing block.

8. An RF coil apparatus as claimed in claim 1 further comprising the patient table in which the base is disposed on top thereof.

9. An RF coil apparatus as claimed in claim 8 wherein the patient table is configured to support the base.

10. A base for supporting a radio-frequency (RF) coil, said RF coil having an electrical cable connected thereto, with one end of said electrical cable being fixed to said RF coil by a first fixing bracket, and said RF coil having an electric cable connected thereto, with one end of said electrical cable being fixed to said RF coil by a first fixing bracket, and said RF coil having a sliding mechanism attached thereto, said base comprising:
a base main body configured to be disposed on top of a patient table, the base main body having a sliding base guide structure therein and a guide cavity therein, wherein said sliding base guide structure is configured to fit said sliding mechanism of said RF coil so that said RF coil slides on said base main body with said electrical cable of said RF coil being accommodated in said guide cavity so as to move in said guide cavity as said RF coil slides on said base main body; and
a second fixing bracket that is configured to fix an opposite end of said RF coil to said base main body, said second fixing bracket being spaced from and positioned relative to said first fixing bracket so as to cause a predetermined length of said electrical cable to project from said base main body.

11. A base as claimed in claim 10 comprising an electric cable drag chain, said electric cable drag chain being disposed in said guide cavity and having one end fixed in the base main body and another end adapted to be fixed to the RF coil, said electric cable being sheathed in said electric cable drag chain in said guide cavity.

12. A base as claimed in claim 10 wherein said base main body has a recess therein configured to receive a bottom of the RF coil therein.

13. A base as claimed in claim 10 wherein said sliding base guide structure is a first sliding base guide structure, having a guiding direction, and wherein said base main body comprises:
a second sliding base guide structure on said base main body, said second sliding base guide structure having a guiding direction that is the same as the guiding direction of said first sliding base guide structure;
a fixing block installed on said base main body so as to slide along said second sliding base guide structure; and
said fixing block being adapted for connection in a fixed manner to said RF coil.

* * * * *